United States Patent [19]

Bernstein et al.

[11] 4,282,375

[45] Aug. 4, 1981

[54] HALOGENATED-NAPHTHALENETRIYL-TRIS(SULFONYLIMINO)-ARYL MULTICARBOXYLIC ACIDS AND SALTS THEREOF

[75] Inventors: Seymour Bernstein, New City; John F. Poletto, Nanuet, both of N.Y.

[73] Assignee: American Cyanamid Company, Stamford, Conn.

[21] Appl. No.: 106,611

[22] Filed: Dec. 26, 1979

[51] Int. Cl.³ .............................................. C07C 143/75
[52] U.S. Cl. ................................ 562/427; 260/501.12; 544/357; 546/186; 424/101; 424/316; 424/319; 560/10
[58] Field of Search .......................................... 562/427

[56] References Cited

U.S. PATENT DOCUMENTS 4,087,613  5/1978  Conrow et al. ...................... 562/427

Primary Examiner—Jane S. Myers

[57] ABSTRACT

Halogenated-naphthalenetriyltris(sulfonylimino)-aryl multicarboxylic acids and salts thereof useful as complement inhibitors.

6 Claims, No Drawings

HALOGENATED-NAPHTHALENETRIYLTRIS(-SULFONYLIMINO)-ARYL MULTICARBOXYLIC ACIDS AND SALTS THEREOF

BACKGROUND OF THE INVENTION

The present invention resides in the concept of certain halogenated-naphthalenetriyltris(sulfonylimino)-aryl multicarboxylic acids and salts thereof as novel compounds and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935-938 (1968); Ann. Rev. Medicine, 19, 1-24 (1968); The Johns Hopkins Med. J., 128, 57-74 (1971); Harvey Lectures, 66, 75-104 (1972); The New England Journal of Medicine, 287, 452-454; 489-495; 545-549; 592-596; 642-646 (1972); Scientific American, 229, (No. 5), 54-66 (1973); Federation Proceedings, 32, 134-137 (1973); Medical World News, Oct. 11, 1974, pp. 53-66; J. Allergy Clin. Immunol., 53, 298-302 (1974); Cold Spring Harbor Conf. Cell Proliferation 2/Proteases Biol. Control/229-241 (1975); Ann. Review of Biochemistry, 44, 697 (1975); Complement in Clinical Medicine, Disease-a-Month, (1975); Complement, Scope, December 1975; Annals of Internal Medicine, 84, 580-593 (1976); "Complement: Mechanisms and Functions," Prentice-Hall, Englewood Cliffs, N.J. (1976); Essays Med. Biochem., 2, 1-35 (1976); Hospital Practice, 12, 33-43 (1977); Perturbation of Complement in Disease, Chap. 15 in Biological Amplification Systems in Immunology (Ed. Day and Good), Plenum, New York and London (1977); Am. J. Clin. Pathology, 68, 647-659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1-8, 1195, 1358-1364, 1482 (1977).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327-339 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415-419; 902-905; 1049-1052; 1053-1056 (1969); Canadian Journal of Biochemistry, 47, 547-552 (1969); The Journal of Immunology, 104, 279-288 (1970); The Journal of Immunology, 106, 241-245 (1971); The Journal of Immunology, 111, 1061-1066 (1973); Biochim. Biophys. Acta, 317, 539-548 (1973); Life Sciences, 13, 351-362 (1973); Journal of Immunology, 113, 584 (1974); Immunology, 26, 819-829 (1974); Journal of Medicinal Chemistry, 17, 1160-1167 (1974); Biochim. Biophys. Res. Comm., 67, 225-263 (1975); Ann. N.Y. Acad. Sci., 256, 441-450 (1975); Journal of Medicinal Chemistry, 19, 634-639, 1079 (1976); Journal of Immunology, 118, 466 (1977); Arch. Int. Pharmacodyn., 226, 281-285 (1977); Biochem. Pharmacol. 26, 325-329 (1977); Journal Pharm. Sci., 66, 1367-1377 (1977); Chem. Pharm. Bull., 25, 1202-1208 (1977); Biochem. Biophys. Acta, 484, 417-422 (1977) and Journal Clin. Microbiology, 5, 278-284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808-812 (1972), 287, 452-454 (1972); Ann. Intern. Med., 84, 580-593 (1976); J. Allergy and Clin. Immunology, 60, 38-40 (1977).

It has also been reported that the drug pentosanpolysulfoester has an anticomplementary activity on human serum, both in vitro and in vivo, as judged by the reduction in total hemolytic complement activity; Pathologie Biologie, 25, 33-36, 25 (2), 105-108, 25 (3), 179-184 (1977).

Publications related to the biological use of Suramin compounds for the purpose of inhibiting the complement system, including humans, as determined by the in vivo and in vitro testing of the blood serum of warm-blooded animals are:

B. Stuber and K. Lang, Arch. Exptl. Path. Pharmacol., 154, 41-49 (1930) [C.A. 25, 3067 (1931)];

F. Klopstock, Zeitschrift für Immunitätsforschung und experimentelle Therapie, 75, 348-354 (1932);

H. J. Schmid, Schweiz. Med. Woch., 96, 1267-1269 (1966);

K. Lauenstein, Bayer-Symposium I, 25-30 (1969);

J. S. C. Fong and R. A. Good, Clin. Exp. Immunol., 10, 127-138 (1972);

V. Eisen and C. Loveday, Br. J. Pharmac., 49, 678-687 (1973);

D. Brackertz and F. Kueppers, Allergol. Et Immunopath., 11, 163-168 (1974);

E. Raepple, H-U. Hill and M. Loos, Immunochemistry, 13 (3), 251-255 (1976).

SUMMARY OF THE INVENTION

This invention is concerned with certain halogenated-naphthalenetriyltris(sulfonylimino)-aryl multicarboxylic acids and salts thereof, and their utility as inhibitors of complement activity in body fluids.

This invention is particularly concerned with compounds having complement inhibiting activity of the general formula (I):

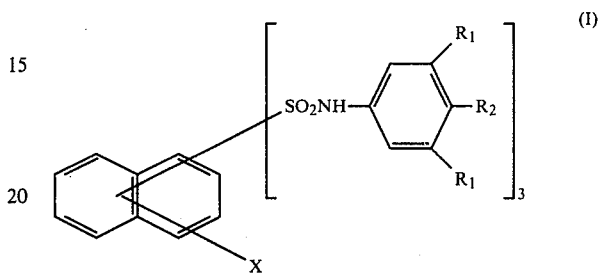

wherein $R_1$ is —$COOR_3$; wherein $R_3$ is selected from the group consisting of hydrogen and a pharmaceutically acceptable salt cation; $R_2$ is selected from the group consisting of hydrogen and —$COOR_3$; and X is halogen.

Of particular interest are the group of compounds encompassed by the above general formula (I), and illustrated by the formulas (II) and (III):

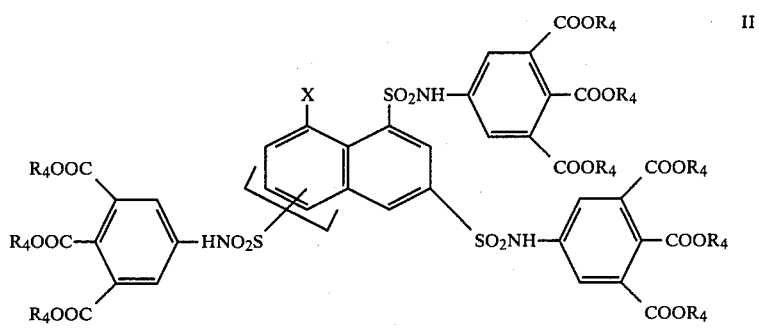

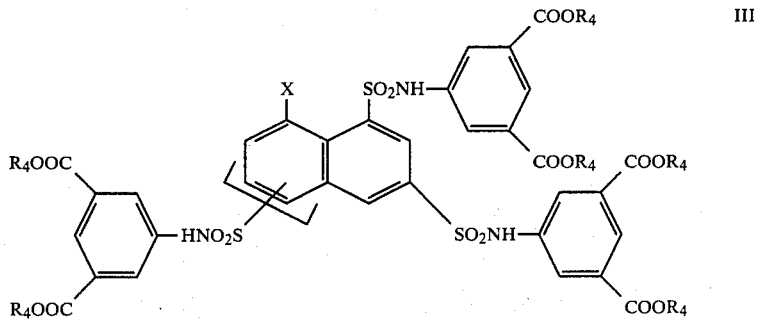

wherein $R_4$ is selected from the group consisting of hydrogen and a pharmaceutically acceptable salt cation; and X is halogen. Operable pharmaceutically acceptable salts include, for example, those of alkali metal, alkaline earth metal, ammonia and substituted ammonia, such as trialkylamines ($C_1$-$C_6$), piperidine, pyrazine, cycloalkylamines ($C_4$-$C_8$), and alkanolamines ($C_2$-$C_6$).

Preferably, the pharmaceutical salt is sodium or potassium.

Representative compounds encompassed within this invention include, for example, 5,5',5''-[(8-chloro-1,3,5-naphthalenetriyl)tris(sulfonylimino)]-tri-1,2,3-benzenetricarboxylic acid, nonasodium salt; 5,5',5''-[(8-chloro-1,3,6-naphthalenetriyl)tris(sulfonylimino)]-tri-1,2,3-benzenetricarboxylic acid, nonasodium salt; 5,5',5''-[(8-chloro-1,3,5-naphthalenetriyl)tris(sulfonylimino)]-tri-1,3-benzenedicarboxylic acid, hexasodium salt; and, 5,5',5''-[(8-chloro-1,3,6-naphthalenetriyl)tris(sulfonylimino)]-tri-1,3-benzenedicarboxylic acid, hexasodium salt.

This invention is also concerned with a method of inhibiting the complement system in a body fluid, such as blood serum, which comprises subjecting the body fluid complement to the action of an effective complement inhibiting amount of a compound of this invention. The method of use aspect of this invention is further concerned with a method of inhibiting the complement system in a warm-blooded animal which comprises administering to said animal an effective complement inhibiting amount of a compound of this invention.

The compounds of this invention find utility as complement inhibitors in body fluids such as blood, plasma, serum, synovial fluid, cerebrospinal fluid, or pathological accumulations of fluid, such as pleural effusion. As such, they may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis.

These compounds may also be used in the treatment of warm-blooded animals having non-immunologic diseases such as paroxysmal nocturnal hemoglobinuria, hereditary angioneurotic edema and inflammatory states induced by the action of bacterial or lysosomal enzymes on the appropriate complement components as for example, inflammation following coronary occlusion. They may also be useful in the treatment of transplant rejection and as blood culture and transport mediums.

DESCRIPTION OF THE INVENTION

The compounds of this invention may be prepared, for example, according to the following illustrative general procedure: Treatment of 8-amino-1,3,5(or 6)-naphthalenetrisulfonic acid, sodium salt with nitrous acid followed by cuprous chloride in hydrochloric acid provides 8-chloro-1,3,5(or 6)-naphthalenetrisulfonic acid, trisodium salt. Treatment of the latter with thionyl chloride provides 8-chloro-1,3,5(or 6)-naphthalenetrisulfonyl chloride. Heating the latter in pyridine with 5-amino-1,2,3-benzenetricarboxylic acid, triphenyl ester provides 5,5',5''-[(8-chloro-1,3,5(or 6)-naphthalenetriyl)tris(sulfonylimino)]-tri-1,2,3-benzenetricarboxylic acid, nonaphenyl ester. Saponification with 2 N sodium hydroxide at room temperature followed by neutralization with acetic acid yields 5,5',5''-[(8-chloro-1,3,5(or 6)-naphthalenetriyl)tris(sulfonylimino)]-tri-1,2,3-benzenetricarboxylic acid, nonasodium salt.

Condensation of 8-chloro-1,3,5(or 6)-naphthalenetrisulfonyl chloride with 5-amino-1,3-benzenedicarboxylic acid bis(2-methoxyethyl)ester produces 5,5',5''-[(8-chloro-1,3,5(or 6)-naphthalenetriyl)tris(sulfonylimino)]-tri-1,3-benzenedicarboxylic acid, hexakis(2-methoxyethyl)ester. Saponification with sodium hydroxide gives 5,5',5''-[(8-chloro-1,3,5(or 6)-naphthalenetriyl)tris(sulfonylimino)]-tri-1,3-benzenedicarboxylic acid, hexasodium salt.

DETAILED DESCRIPTION OF THE INVENTION

The following examples describe in detail the preparation and formulation of representative compounds of the present invention.

EXAMPLE 1

8-Chloro-1,3,5-naphthalenetrisulfonic acid, trisodium salt

To an ice-cold stirred mixture of 20 g. of 8-amino-1,3,5-naphthalenetrisulfonic acid, trisodium salt in 20 ml. of concentrated hydrochloric acid and 80 ml. of water is added dropwise a solution of 3.5 g. of sodium nitrite in 15 ml. of water. The resulting solution is stirred at 0° C. for 20 minutes then is added slowly to a stirred solution of 10 g. of cuprous chloride in 30 ml. of concentrated hydrochloric acid, and stirring is continued for one hour at room temperature. The reaction mixture is heated to 60° C., cooled, and treated with 32 g. of sodium carbonate. The precipitated solid is filtered and washed with water. Concentration of the filtrate affords 17.4 g. of the desired compound in several crops. The combined solid is reprecipitated from 50 ml. of water with 250 ml. of ethanol to give 11.1 g. of the 8-chloro compound as a light tan solid.

Following the above procedure employing cuprous bromide and hydrobromic acid provides 8-bromo-1,3,5-naphthalenetrisulfonic acid, trisodium salt.

Treatment of the above described diazonium salt with potassium iodide provides 8-iodo-1,3,5-naphthalenetrisulfonic acid, trisodium salt.

EXAMPLE 2

8-Chloro-1,3,5-naphthalenetrisulfonyl chloride

A stirred mixture of 11 g. of 8-chloro-1,3,5-naphthalenetrisulfonic acid, trisodium salt in 100 ml. of thionyl chloride and 1.1 ml. of N,N-dimethylformamide is heated at reflux for 3 hours. The hot mixture is filtered, and the separated inorganic solid is washed with hot acetonitrile. The combined filtrates are evaporated, and the residue is recrystallized from acetonitrile to give 6 g. of yellow crystals, m.p. 165°–166° C.

Similarly, 8-bromo-1,3,5-naphthalenetrisulfonyl chloride and 8-iodo-1,3,5-naphthalenetrisulfonyl chloride are prepared.

EXAMPLE 3

5,5',5''-[(8-Chloro-1,3,5-naphthalenetriyl)tris(sulfonylimino)]-tri-1,2,3-benzenetricarboxylic acid, nonaphenyl ester To a stirred solution of 13.6 g. of 5-amino-1,2,3-benzenetricarboxylic acid, triphenyl ester (U.S. Pat. No. 4,087,613) in 45 ml. of dry pyridine is added 4.58 g. of 8-chloro-1,3,5-naphthalenetrisulfonyl chloride, and the mixture is heated at 60°–70° C. for three hours. The cooled solution is added slowly with vigorous stirring to 300 ml. of ice-water, and the resulting solid is collected by filtration, washed with water, and dried. The solid is dissolved in methylene chloride, washed with water, and dried. The extract is concentrated to a volume of 80 ml. and passed through a bed of hydrous magnesium silicate. Evaporation of the filtrate with the addition of ether gives a solid, which is purified by chromatography on silica gel giving 7.8 g. of a light yellow solid.

Similarly, 5,5',5''-[(8-bromo-1,3,5-naphthalenetriyl)tris(sulfonylimino)]-tri-1,2,3-benzenetricarboxylic acid, nonaphenyl ester, and 5,5',5''-[(8-iodo-1,3,5-naphthalenetriyl)tris(sulfonylimino)]-tri-1,2,3-benzenetricarboxylic acid, nonaphenyl ester are prepared.

EXAMPLE 4

5,5',5''-[(Chloro-1,3,5-naphthalenetriyl)tris(sulfonylimino)]-tri-1,2,3-benzenetricarboxylic acid, nonasodium salt A solution of 7.2 g of 5,5',5''-[(8-chloro-1,3,5-naphthalenetriyl)tris(sulfonylimino)]-tri-1,2,3-benzenetricarboxylic acid, nonaphenyl ester in 54 ml. of 2 N sodium hydroxide is stirred at room temperature for 45 minutes. The solution is neutralized with acetic acid, concentrated to a volume of 60 ml., and poured with vigorous stirring into 800 ml. of ethanol. The solid is collected by filtration, washed with ethanol and ether, and dried. Reprecipitation of the solid from 40 ml. of water with 600 ml. of ethanol affords 5.13 g. of product as a light yellow solid.

Similarly, 5,5',5''-[(8-bromo-1,3,5-naphthalenetriyl)tris(sulfonylimino)]-tri-1,2,3-benzenetricarboxylic acid, nonasodium salt, and 5,5',5''-[(8-iodo-1,3,5-naphthalenetriyl)tris(sulfonylimino)]-tri-1,2,3-benzenetricarboxylic acid, nonasodium salt are prepared.

EXAMPLE 5

Isomeric 5,5',5''-[(Halo-naphthalenetriyl)tris(sulfonylimino)]-tri-1,2,3-benzenetricarboxylic acid, nonasodium salt Following the procedure of Examples 1–4, the aminonaphthalene starting materials may be:
2-amino-1,3,7-naphthalenetrisulfonic acid
4-amino-1,3,6-naphthalenetrisulfonic acid
4-amino-1,3,7-naphthalenetrisulfonic acid
5-amino-1,3,6-naphthalenetrisulfonic acid
5-amino-1,3,7-naphthalenetrisulfonic acid
6-amino-1,3,5-naphthalenetrisulfonic acid
6-amino-1,3,7-naphthalenetrisulfonic acid
7-amino-1,3,5-naphthalenetrisulfonic acid
7-amino-1,3,6-naphthalenetrisulfonic acid
7,amino-2,3,6-naphthalenetrisulfonic acid
8-amino-1,3,6-naphthalenetrisulfonic acid
which provide the following compounds, where halo represents a member of the halogen family, such as, chlorine, bromine and iodine:

5,5',5''-[(2-halo-1,3,7-naphthalenetriyl)tris(sulfonylimino)]-tri-1,2,3-benzenetricarboxylic acid, nonasodium salt
5,5',5''-[(4-halo-1,3,6-naphthalenetriyl)tris(sulfonylimino)]-tri-1,2,3-benzenetricarboxylic acid, nonasodium salt
5,5',5''-[(4-halo-1,3,7-naphthalenetriyl)tris(sulfonylimino)]-tri-1,2,3-benzenetricarboxylic acid, nonasodium salt
5,5',5''-[(5-halo-1,3,6-naphthalenetriyl)tris(sulfonylimino)]-tri-1,2,3-benzenetricarboxylic acid, nonasodium salt
5,5',5''-[(5-halo-1,3,7-naphthalenetriyl)tris(sulfonylimino)]-tris-1,2,3-benzenetricarboxylic acid, nonasodium salt
5,5',5''-[(6-halo-1,3,5-naphthalenetriyl)tris(sulfonylimino)]-tri-1,2,3-benzenetricarboxylic acid, nonasodium salt
5,5',5''-[(6-halo-1,3,7-naphthalenetriyl)tris(sulfonylimino)]-tri-1,2,3-benzenetricarboxylic acid, nonasodium salt
5,5',5''-[(7-halo-1,3,5-naphthalenetriyl)tris(sulfonylimino)]-tri-1,2,3-benzenetricarboxylic acid, nonasodium salt
5,5',5''-[(7-halo-1,3,6-naphthalenetriyl)tris(sulfonylimino)]-tri-1,2,3-benzenetricarboxylic acid, nonasodium salt
5,5',5''-[(7-halo-2,3,6-naphthalenetriyl)tris(sulfonylimino)]-tri-1,2,3-benzenetricarboxylic acid, nonasodium salt
5,5',5''-[(8-halo-1,3,6-naphthalenetriyl)tris(sulfonylimino)]-tri-1,2,3-benzenetricarboxylic acid, nonasodium salt

EXAMPLE 6

5,5',5''-[(8-Chloro-1,3,5-naphthalenetriyl)tris(sulfonylimino)]-tri-1,3-benzenedicarboxylic acid, hexakis(2-methoxyethyl)ester Following the procedure of Example 3, reaction of 8-chloro-1,3,5-naphthalenetrisulfonyl chloride with 5-amino-1,3-benzenedicarboxylic acid, bis(2-methoxyethyl)ester (U.S. Pat. No. 4,087,613) provides the product of the Example.

EXAMPLE 7

5,5',5''-[(8-Chloro-1,3,5-naphthalenetriyl)tris(sulfonylimino)]-tri-1,3-benzenedicarboxylic acid, hexasodium salt A mixture of 9.05 g. of the product of Example 6 and 45 ml. of 2 N sodium hydroxide is stirred at room temperature for 45 minutes. The solution is filtered, the filtrate is neutralized with 2.5 ml. of glacial acetic acid, and diluted with 250 ml. of ethanol. The product formed is collected by filtration, washed with ethanol followed by ether, and dried to give the product of the Example.

EXAMPLE 8

Isomeric 5,5',5''-[(Halo-naphthalenetriyl)tris(sulfonylimino)]-tri-1,3-benzenedicarboxylic acid, hexasodium salt Following the procedure of Examples 6–7, the aminonaphthalene starting materials may be:
2-amino-1,3,7-naphthalenetrisulfonic acid
4-amino-1,3,6-naphthalenetrisulfonic acid
4-amino-1,3,7-naphthalenetrisulfonic acid
5-amino-1,3,6-naphthalenetrisulfonic acid
5-amino-1,3,7-naphthalenetrisulfonic acid
6-amino-1,3,5-naphthalenetrisulfonic acid
6-amino-1,3,7-naphthalenetrisulfonic acid
7-amino-1,3,5-naphthalenetrisulfonic acid
7-amino-1,3,6-naphthalenetrisulfonic acid
7-amino-2,3,6-naphthalenetrisulfonic acid
8-amino-1,3,6-naphthalenetrisulfonic acid
which provide the following compounds, where halo represents a member of the halogen family, such as, chlorine, bromine, and iodine:

5,5',5''-[(2-halo-1,3,7-naphthalenetriyl)tris(sulfonylimino)]-tri-1,3-benzenedicarboxylic acid, hexasodium salt 5,5',5''-[(4-halo-1,3,6-naphthalenetriyl)tris(sulfonylimino)]-tri-1,3-benzenedicarboxylic acid, hexasodium salt 5,5',5''-[(4-halo-1,3,7-naphthalenetriyl)tris(sulfonylimino)]-tri-1,3-benzenedicarboxylic acid, hexasodium salt 5,5',5''-[(5-halo-1,3,6-naphthalenetriyl)tris(sulfonylimino)]-tri-1,3-benzenedicarboxylic acid, hexasodium salt 5,5',5''-[(5-halo-1,3,7-naphthalenetriyl)tris(sulfonylimino)]-tri-1,3-benzenedicarboxylic acid, hexasodium salt 5,5',5''-[(6-halo-1,3,5-naphthalenetriyl)tris(sulfonylimino)]-tri-1,3-benzenedicarboxylic acid, hexasodium salt 5,5',5''-[(6-halo-1,3,7-naphthalenetriyl)tris(sulfonylimino)]-tri-1,3-benzenedicarboxylic acid, hexasodium salt 5,5',5''-[(7-halo-1,3,5-naphthalenetriyl)tris(sulfonylimino)]-tri-1,3-benzenedicarboxylic acid, hexasodium salt 5,5',5''-[(7-halo-1,3,6-naphthalenetriyl)tris(sulfonylimino)]-tri-1,3-benzenedicarboxylic acid, hexasodium salt 5,5',5''-[(7-halo-2,3,6-naphthalenetriyl)tris(sulfonylimino)]-tri-1,3-benzenedicarboxylic acid, hexasodium salt 5,5',5''-[(8-halo-1,3,6-naphthalenetriyl)tris(sulfonylimino)]-tri-1,3-benzenedicarboxylic acid, hexasodium salt

EXAMPLE 9

Preparation of Compressed Tablet

| Ingredient | mg/Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 10

Preparation of Compressed Tablet - Sustained Action

| Ingredient | mg/Tablet |
| --- | --- |
| Active Compound as Aluminum Lake*, Micronized | 0.5–500(as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 11

Preparation of Hard Shell Capsule

| Ingredient | mg/Capsule |
| --- | --- |
| Active Compound | 0.5–500 |
| Lactose, Spray Dried | qs |
| Magnesium Stearate | 1–10 |

EXAMPLE 12

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 13

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 14

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 15

Preparation of Injectable Solution

| Ingredient | % W/V |
| --- | --- |
| Active Compound | 0.05–5 |
| Benzyl Alcohol N.F. | 0.9 |
| Water for Injection | 100.0 |

EXAMPLE 16

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 17

Preparation of Intra-Articular Product

| Ingredient | Amount |
| --- | --- |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |

-continued

| Preparation of Intra-Articular Product | |
|---|---|
| Ingredient | Amount |
| Water for Injection qs ad | 100% |

EXAMPLE 18

| Preparation of Injectable Depo Suspension | |
|---|---|
| Ingredient | % W/V |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 19

| Preparation of Dental Paste | |
|---|---|
| Ingredient | % W/W |
| Active Compound | 0.05–5 |
| Zinc Oxide | 15 |
| Polyethylene Glycol 4000 USP | 50 |
| Distilled Water qs. | 100 |

EXAMPLE 20

| Preparation of Dental Ointment | |
|---|---|
| Ingredient | % W/W |
| Active compound | 0.05–5 |
| Petrolatum, White USP qs | 100 |

EXAMPLE 21

| Preparation of Dental Cream | |
|---|---|
| Ingredient | % W/W |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 22

| Preparation of Topical Cream | |
|---|---|
| Ingredient | % W/W |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs. | 100 |

EXAMPLE 23

| Preparation of Topical Ointment | |
|---|---|
| Ingredient | % W/W |
| Active Compound | 0.05–5 |
| Cholesterol | 3 |
| Stearyl Alcohol | 3 |
| White Wax | 8 |
| Petrolatum, White USP qs | 100 |

EXAMPLE 24

| Preparation of Spray Lotion (non-Aerosol) | |
|---|---|
| Ingredient | % W/W |
| Active Compound | 0.05–5 |
| Isopropyl Myristate | 20 |
| Alcohol (Denatured) qs | 100 |

EXAMPLE 25

| Preparation of Buccal Tablet | |
|---|---|
| Ingredient | g/Tablet |
| Active Ingredient | 0.00325 |
| 6 × Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 26

| Preparation of Lozenge | |
|---|---|
| Ingredient | g/Lozenge |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg./kg./day, or every six hours for more rapidly excreted salts, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg./kg. to about 100 mg./kg. of body weight of animal per day. The usual daily dosage for a 70 kg. subject may vary from about 350 mg. to about 3.5 g. Unit doses of the acid or salt can contain from about 0.5 mg. to about 500 mg.

While in general the sodium salts of the acids of the invention are suitable for parenteral use, other salts may also be prepared, such as those of primary amines, e.g., ethylamine; secondary amines, e.g., diethylamine or diethanolamine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of approriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg./kg. is then reported, unless otherwise stated; (v) Forssman Shock Test—Lethal shock is produced in guinea pigs by an i.v. injection of anti-Forssman antiserum and the haromic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; (vii) Cap 50 Test—Here, appropriate amounts of the test compound are added to a pool of guinea pig serum in vitro, after which the undiluted serum capillary tube assay referred to above is run. The concentration of compound inhibiting 50% is reported; (viii) Guinea Pig Intraperitoneal Test (GPIP)—Guinea Pigs weighing about 300 g. are dosed intraperitoneally (i.p.) with 200 mg./kg. of the test compound dissolved in saline and adjusted to pH 7-8. Approximately 0.4 ml. blood samples, taken by orbital sinus puncture 30 minutes and one hour after injections, are collected directly into centrifuge tubes; 5 ml. blood samples, taken by decapitation 2 hours after injection are collected directly into diSPo ® beakers. The samples were allowed to clot, centrifuged, and the resultant sera are assayed for complement activity using the capillary complement assay. Percent inhibition is calculated by comparison with simultaneous controls. The results appear in Table I together with results of Test Code 026, 035, 036, Cap 50 and % inhibition. Table I shows that the principal compound of the invention possesses highly significant in vitro and in vivo complement inhibiting activity in warm-blooded animals.

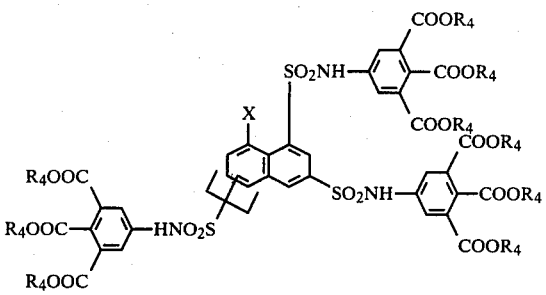

wherein $R_4$ is selected from the group consisting of hydrogen and a pharmaceutically acceptable salt cation; and X is halogen.

2. A compound of the formula:

| | BIOLOGICAL ACTIVITIES | | | | | | |
|---|---|---|---|---|---|---|---|
| | | | | | In Vivo Activity (Guinea Pig) % Inhibition | | |
| | Cl | C-Late | Shunt Inhibition | Intraperitoneal | | | |
| | 026* | 035* | 036* | | Time (Minutes) | | |
| Compound | Wells | Wells | Wells | CaP 50* | 30 | 60 | 120 |
| 5,5',5''-[(8-Chloro-1,3,5-naphthalenetriyl)tris(sulfonylimino)]-tri-1,2,3-benzenetricarboxylic acid, nonasodium salt | +7** | +2** | +5** | 82 | −75 | −69 | 75 |

*Code designation for tests employed as referred herein.
**Activity in wells, a serial dilution assay. Higher well number indicates higher activity. The serial dilutions are two-fold.

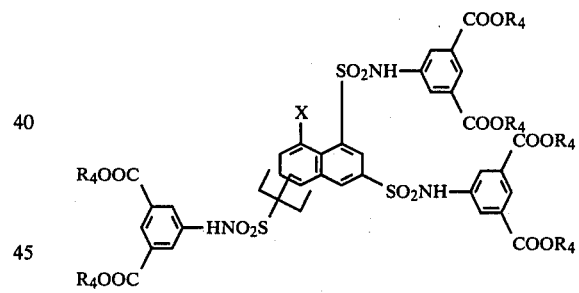

wherein $R_4$ is selected from the group consisting of hydrogen and a pharmaceutically acceptable salt cation; and X is halogen.

3. The compound according to claim 1, 5,5',5''-[(8-chloro-1,3,5-naphthalenetriyl)tris(sulfonylimino)]-tri-1,2,3-benzenetricarboxylic acid, nonasodium salt.

4. The compound according to claim 1, 5,5',5''-[(8-chloro-1,3,6-naphthalenetriyl)tris(sulfonylimino)]-tri-1,2,3-benzenetricarboxylic acid, nonasodium salt.

5. The compound according to claim 2, 5,5',5''-[(8-chloro-1,3,5-naphthalenetriyl)tris(sulfonylimino)]-tri-1,3-benzenedicarboxylic acid, hexasodium salt.

6. The compound according to claim 2, 5,5',5''-[(8-chloro-1,3,6-naphthalenetriyl)tris(sulfonylimino)]-tri-1,3-benzenedicarboxylic acid, hexasodium salt.

We claim:

1. A compound of the formula:

* * * * *